US012285016B2

(12) United States Patent
Bentley et al.

(10) Patent No.: US 12,285,016 B2
(45) Date of Patent: Apr. 29, 2025

(54) HYDROGEN PEROXIDE DISINFECTANT COMPOSITION

(71) Applicant: ARXADA, LLC, Morristown, NJ (US)

(72) Inventors: Marcus Allen Bentley, Morristown, NJ (US); Xiao Jiang, Montvale, NJ (US); Mark Garrison, Allendale, NJ (US)

(73) Assignee: ARXADA, LLC, Morristown, NJ (US)

( * ) Notice: Subject to any disclaimer, the term of this patent is extended or adjusted under 35 U.S.C. 154(b) by 958 days.

(21) Appl. No.: 17/423,134

(22) PCT Filed: Feb. 26, 2020

(86) PCT No.: PCT/US2020/019906
§ 371 (c)(1),
(2) Date: Jul. 15, 2021

(87) PCT Pub. No.: WO2020/176623
PCT Pub. Date: Sep. 3, 2020

(65) Prior Publication Data
US 2022/0183297 A1 Jun. 16, 2022

Related U.S. Application Data

(60) Provisional application No. 62/811,293, filed on Feb. 27, 2019.

(51) Int. Cl.
A61L 2/00 (2006.01)
A01N 31/02 (2006.01)
A01N 59/00 (2006.01)
A01P 1/00 (2006.01)
A61L 2/18 (2006.01)
A61L 9/00 (2006.01)
A61L 9/015 (2006.01)
C09K 3/22 (2006.01)
A61L 101/34 (2006.01)
A61L 101/38 (2006.01)

(52) U.S. Cl.
CPC ............. A01N 59/00 (2013.01); A01N 31/02 (2013.01); A01P 1/00 (2021.08); A61L 2/186 (2013.01); A61L 2101/34 (2020.08); A61L 2101/38 (2020.08); A61L 2202/26 (2013.01)

(58) Field of Classification Search
CPC .. C11D 1/00; A61K 7/32; A61K 31/60; A61L 9/015; A61L 9/14

USPC ...... 422/28, 32, 34; 424/76.2, 605; 510/214, 510/372; 442/59
See application file for complete search history.

(56) References Cited

U.S. PATENT DOCUMENTS

| 5,891,392 | A | 4/1999 | Monticello et al. |
| 7,144,846 | B2 | 12/2006 | Keller et al. |
| 7,354,604 | B2 | 4/2008 | Ramirez et al. |
| 7,806,984 | B2 | 10/2010 | Kuibira et al. |
| 9,765,287 | B2 | 9/2017 | Som et al. |
| 9,789,216 | B2 | 10/2017 | Berentsveig et al. |
| 10,010,072 | B2 | 7/2018 | Kritzler |
| 10,238,108 | B2 | 3/2019 | Griese |
| 10,450,535 | B2 | 10/2019 | Ahmadpour |
| 11,312,922 | B2 | 4/2022 | Bakken |
| 2005/0058719 | A1* | 3/2005 | Ramirez ................ A01N 59/00 424/70.13 |
| 2005/0256018 | A1 | 11/2005 | Keller et al. |
| 2006/0285995 | A1 | 12/2006 | Hobbs et al. |
| 2016/0074549 | A1 | 3/2016 | Lei et al. |
| 2018/0343859 | A1 | 12/2018 | Jiang et al. |
| 2019/0322964 | A1 | 10/2019 | Ahmadpour |

FOREIGN PATENT DOCUMENTS

| CL | 199501444 | 7/1996 |
| CL | 52012 | 2/2012 |
| CL | 201502419 | 8/2016 |
| WO | WO9609761 | 4/1996 |
| WO | WO2005113739 | 12/2005 |

OTHER PUBLICATIONS

International Preliminary Report on Patentability dated Aug. 25, 2021, 9 pages.
Columbia Patent Application No. 202102232 Office Action and Search Report dated Nov. 2, 2022, 28 pages.
International Search Report and Written Opinion for PCT/US2020/019906 dated May 14, 2020, 12 pages.

* cited by examiner

Primary Examiner — Monzer R Chorbaji
(74) Attorney, Agent, or Firm — Dority & Manning, P.A.

(57) ABSTRACT

The present invention herein provides a disinfectant composition containing a) an effective amount of a hydrogen peroxide source, b) a blend of at least one aromatic alcohol and at least one glycol or glycol ether, c) at least one nonionic and/or anionic surfactant and d) at least one acid. Furthermore a method of using the disinfectant composition is also provided, whereby the composition can be applied to any surface and effectively kill a majority of tuberculosis and/or *M. terrae* microbes; resulting in a >5 log reduction at a contact time of 5 minutes or less.

24 Claims, No Drawings

HYDROGEN PEROXIDE DISINFECTANT COMPOSITION

CROSS REFERENCE TO RELATED APPLICATIONS

This application is the U.S. National Stage entry of International Application Number PCT/US2020/019906 filed under the Patent Cooperation Treaty having a filing date of Feb. 26, 2020, which claims priority to U.S. Provisional Application No. 62/811,293 having a filing date of Feb. 27, 2019, which are incorporated herein by reference.

FIELD OF INVENTION

The disclosure relates to a disinfectant composition containing hydrogen peroxide and a novel solvent system effective against tuberculosis containing bacteria.

BACKGROUND OF THE INVENTION

Among the known disinfectants and antimicrobials, hydrogen peroxide is a preferred choice, not only due to its potential as a biocide, but also due to its low toxicity as it decomposes into nontoxic oxygen and water. Additionally, hydrogen peroxide is the ideal active for disinfectant formulations on non-hard porous surfaces because it has an inherent ability to kill a broad range of micro-organism and it has a low toxicity product.

Unfortunately, hydrogen peroxide alone can't kill higher level organisms like tuberculosis and is especially harder to exhibit shorter kill times (<5 minutes) are desired. Hydrogen peroxide is therefore not very efficient by itself, against certain organisms. It doesn't show the efficacy against tuberculosis-causing bacteria even at a high active level with long contact time. Additionally, most commercial hydrogen peroxide based products are not able to kill tuberculosis-causing bacteria (TB) on hard surfaces within short contact time.

There is a need in the art to provide the hospital disinfectant market with disinfectant products that are efficient at killing tuberculosis-causing bacteria and provide rapid disinfecting properties after application to a surface.

SUMMARY OF THE INVENTION

It has now been surprisingly found that the combination of hydrogen peroxide and a novel solvent system is effective against tuberculosis containing bacteria, having an effective kill of >5 log reduction against tuberculosis causing bacteria, at contact kill time of 5 minutes or less.

The present disclosure provides an answer to that need of having a disinfectant composition, containing hydrogen peroxide, effective against tuberculosis-causing bacteria even at a high active level. The present invention provides a disinfectant composition, containing an acidified hydrogen peroxide solution at a pH 0 to 5, and a novel solvent system, effective against tuberculosis and/or *M. terrae*. The composition provides an effective kill of >5 log reduction against tuberculosis causing bacteria, at contact kill time of 5 minutes or less.

In one embodiment, the present invention provides a disinfectant composition comprising a) an effective amount of a hydrogen peroxide source, b) at least one aromatic alcohol c) at least one glycol or glycol ether, d) at least one nonionic and/or anionic surfactant and e) at least one acid.

In one embodiment, the hydrogen peroxide source comprises a hydrogen peroxide solution, sodium percarbonate, potassium percarbonate, sodium perborate, potassium perborate, hydrogen peroxide urea or peroxide salts, hydrated salts thereof, or combinations thereof.

In one embodiment, the concentration of the hydrogen peroxide source is from 0.01 w/w % to about 90 w/w % of the total weight of the composition.

In one embodiment, at least one aromatic alcohol is present comprising, anisyl alcohol, benzyl alcohol, phenoxyethanol, vanillyl alcohol, phenols, polyphenols, derivatives thereof, or salts thereof.

In another embodiment, at least one glycol or glycol ether is present, comprising butylene glycol, diethylene glycol monomethyl ether, diethylene glycol monobutyl ether, diethylene glycol monoethyl ether, diethylene glycol mono-n-butyl ether, dipropylene glycol butyl ether, dipropylene glycol methyl ether, diethylene glycol propyl ether, ethylene glycol, ethylene glycol monomethyl ether, ethylene glycol monoethyl ether, ethylene glycol monopropyl ether, ethylene glycol monoisopropyl ether, ethylene glycol monobutyl ether, ethylene glycol dimethyl ether, ethylene glycol diethyl ether, ethylene glycol dibutyl ether, propylene glycol, propylene glycol n-butyl ether, tripropylene glycol methyl ether, triethylene glycol monobutyl ether, or combinations thereof.

In one particular embodiment, at least one aromatic alcohol and at least one glycol or glycol ether is present as a blend, wherein the blend is in a ratio of 1:100 to 100:1.

In one embodiment, the blend of at least one aromatic alcohol and at least one glycol or glycol ether is present in an amount from about 0.01 w/w %-90 w/w % of the total composition.

In one particular embodiment, at least one non-ionic surfactant and/or anionic surfactants is present in an amount, wherein the total amount of surfactants present, is in an amount from 0.01 w/w %-15 w/w % of the total composition.

In another embodiment, at least one acid comprises an organic acid, inorganic acid, carboxylic acid, mineral acid, non-surfactant sulfonic acid, or salt thereof.

In one embodiment, the total amount of the acids is present in an amount from 0.01 w/w %-15 w/w % of the total composition.

In yet another embodiment, the composition further comprises a peroxide stabilizer and/or chelating agent; wherein the stabilizer and/or chelating agent is present in an amount from 0.01 w/w %-5 w/w %, based on the weight of the total composition.

In one embodiment, the composition is one having a pH of about 0 to about 5.

In yet another embodiment, the composition further comprises a second biocidal agent present in an amount from 0.01 w/w %-20 w/w %.

In one particular embodiment, the composition comprises a concentrate and in another embodiment, the composition comprises a ready-to-use composition upon dilution with an aqueous solvent, non-aqueous solvent or mixture thereof.

In a further embodiment, the composition is effective against one or more micro-organism comprising gram positive bacteria, gram negative bacteria, viruses, fungi, mildew, mold or combinations thereof.

In another embodiment, the composition is effective against tuberculosis and/or *M. terrae*.

In one particular embodiment, the composition provides an effective kill of >5 log reduction at contact time of 5 minutes or less.

In one particular embodiment, the invention provides a disinfectant composition, according to present invention, containing a) an effective amount of a hydrogen peroxide source, wherein said source comprises a hydrogen peroxide solution; b) at least one aromatic alcohol wherein said alcohol comprises, benzyl alcohol and/or phenoxyethanol; c) at least one glycol or glycol ether, wherein said glycol comprises diethylene glycol monobutyl ether, triethylene glycol monobutyl ether; d) at least one nonionic and/or anionic surfactant, wherein said surfactant comprises $C_{12}$-$C_{15}$, Ethoxylated alcohol, $C_{12}$-$C_{14}$ secondary Ethoxylated alcohol 70%, 2-ethyl hexanol EO-PO nonionic surfactant, Capryly/Decyl Glucoside, and/or linear alkylbenzene sulfonic acid; and e) at least one acid, wherein said acid comprises methanesulfonic acid; and wherein the composition is effective against tuberculosis and/or M. terrae.

In another embodiment, the invention provides a method for disinfecting a surface from tuberculosis and/or M. terrae, wherein said method comprises adding an effective amount of the disinfectant composition, according to the present invention, and applying the composition to a surface, in an amount to effectively kill a majority of the microbes located on said surface.

In another embodiment, the method comprises a disinfectant composition to inhibit growth of one or more microorganisms therein and/or to reduce the number of live micro-organisms.

In one embodiment, the surface is a hard or soft surface comprising a floor, a wall, a countertop, an appliance, a fixture, fabric, textile or other hard or soft surfaces.

In yet a further embodiment, the invention provides a method for enhancing the disinfectant properties of a hydrogen peroxide source, wherein said method comprises adding a sufficient amount of b) at least one aromatic alcohol; c) at least one glycol or glycol ether; d) at least one nonionic and/or anionic surfactant; and e) at least one acid; with a hydrogen peroxide source and wherein the composition is applied to a surface.

In another embodiment, the invention provides a disinfection composition comprising b) at least one aromatic alcohol; c) at least one glycol or glycol ether; d) at least one nonionic and/or anionic surfactant; and e) at least one acid; wherein the composition is effective against tuberculosis and/or M. terrae; and wherein the composition may be diluted with a solvent to form a ready-to-use composition.

In one particular embodiment, the invention provides a two-part disinfectant, comprising: a first container including a) a biocidal amount of hydrogen peroxide, and a solvent; and a second container including b) at least one aromatic alcohol; c) at least one glycol or glycol ether; d) at least one nonionic and/or anionic surfactant; and e) at least one acid.

In one embodiment, the two part disinfectant is effective against tuberculosis and/or M. terrae, wherein said disinfectant provides a >5 log reduction at a contact time of 5 minutes or less.

In yet a further embodiment, the invention provides an additive for a disinfectant composition comprising b) at least one aromatic alcohol; c) at least one glycol or glycol ether; d) at least one nonionic and/or anionic surfactant; and e) at least one acid; wherein said additive enhances the disinfecting properties of said composition when combined with a disinfecting active.

In one embodiment, the disinfecting active comprises a hydrogen peroxide solution, alcohol, bleach, organic acid, or phenol.

DETAILED DESCRIPTION

The present invention provides a disinfectant composition containing hydrogen peroxide source effective against tuberculosis and/or M. terrae having a >5 log reduction at a contact time of 5 minutes or less. These and other aspects will become apparent when reading the detailed description of the invention.

The term "effective amount" herein refers any amount that would bring about the desired effect, based on the known purpose and function of the ingredient and application of the composition. What constitutes an effective amount will be determinable by the person of ordinary skill in the art without having to engage in inventive experimentation.

It has now been surprisingly found that combining an acidified hydrogen peroxide solution having a pH 0 to 5, and a novel organic solvent system; provides the composition exhibiting a >5 log reduction against M. terrae and/or tuberculosis at a contact time of 5 minutes or less.

One aspect of the present invention provides a disinfectant composition containing a) an effective amount of a hydrogen peroxide source, b) at least one aromatic alcohol c) at least one glycol or glycol ether, d) at least one nonionic and/or anionic surfactant and e) at least one acid.

The disinfectant composition as described in the present invention, is a concentrate and/or a ready-to use composition.

Typically, the hydrogen peroxide sources include, but are not limited to hydrogen peroxide solutions, percarbonate salts (i.e. sodium percarbonate, potassium percarbonate), perborate salts (i.e. sodium perborate, potassium perborate), hydrogen peroxide urea or peroxide salts, hydrated salts thereof, or combinations thereof, and the like.

Typically, the concentration of the hydrogen peroxide source is from 0.01% to about 90 w/w % of the total weight of the composition. The hydrogen peroxide source present in the disinfectant composition, is typically present in an amount from 0.1 w/w % to about 50 w/w %, based on the total weight of the composition. Suitably, the concentration of the hydrogen peroxide source is from 0.5 w/w % to about 20 w/w %, based on the total weight of the composition. Desirably, the concentration of the hydrogen peroxide source is from 0.01 w/w % to about 15 w/w % of the total weight of the composition. In ready-to-use forms, typically the hydrogen peroxide amount is from 0.01 w/w %-15 w/w %; suitably from 0.1 w/w %-10 w/w % or desirably from 0.01 w/w %-7 w/w % of the total composition.

Typically, at least one aromatic alcohol is present in the composition. Examples includes, but are not limited to, anisyl alcohol, benzyl alcohol, phenoxyethanol, vanillyl alcohol, phenols, polyphenols, derivatives thereof, or salts thereof, and the like. Suitably, at least one aromatic alcohol includes benzyl alcohol and/or phenoxyethanol.

Typically, at least one aromatic alcohol is present in an amount from about 0.01 w/w %-50 w/w %, based on the weight of total composition. Suitably, at least one aromatic alcohol is present in an amount from about 0.1 w/w %-25 w/w % and desirably in an amount from about 0.1 w/w %-15%, based on the weight of the total composition.

Typically, examples of glycols or glycol ether include, but are not limited to, at least one glycol or glycol ether comprises butylene glycol, diethylene glycol monomethyl ether, diethylene glycol monobutyl ether, diethylene glycol monoethyl ether, diethylene glycol mono-n-butyl ether, dipropylene glycol butyl ether, dipropylene glycol methyl ether, diethylene glycol propyl ether, ethylene glycol, ethylene glycol monomethyl ether, ethylene glycol monoethyl ether, ethylene glycol monopropyl ether, ethylene glycol monoisopropyl ether, ethylene glycol monobutyl ether, ethylene glycol dimethyl ether, ethylene glycol diethyl ether, ethylene glycol dibutyl ether, propylene glycol, propylene glycol n-butyl ether, tripropylene glycol methyl ether, triethylene glycol monobutyl ether, or combinations thereof, and the like. Suitably, at least one glycol or glycol ether includes diethylene glycol monobutyl ether, and/or triethylene glycol monobutyl ether.

Typically, at least one glycol or glycol ether is present in an amount from about 0.01 w/w %-50 w/w %, based on the weight of total composition. Suitably, at least one glycol or glycol ether is present in an amount from about 0.1 w/w %-25 w/w %; or desirably in an amount from about 0.1 w/w %-15%, based on the weight of the total composition.

If desired, the composition contains a novel solvent system, whereby the system is a) at least one aromatic alcohol, and/or b) at least one glycol or glycol ether or c) a blend of at least one aromatic alcohol and at least one glycol or glycol ether. If desired, typically, the blend of at least one aromatic alcohol and at least one glycol or glycol ether is present in a ratio of 1:100 to 100:1. Suitably, the blend is in a ratio of 1:50 to 50:1; or desirably the blend is in a ratio of 1:20 to 20:1.

Typically, the blend of at least one aromatic alcohol and at least one glycol or glycol ether is present in an amount from about 0.01 w/w %-90 w/w % of the total composition. Suitably, the blend is present in an amount from about 0.1 w/w %-75 w/w % or suitably the blend is present in an amount from about 0.1 w/w %-50 w/w %, based on the weight of the total composition.

For example, the disinfectant composition contains a blend of benzyl alcohol and/or phenoxyethanol with diethylene glycol monobutyl ether and/or triethylene glycol monobutyl ether in a ratio of 1:100 to 100:1; whereby the typical total amount of the blend is in an amount from about 0.01 w/w %-90 w/w %, based on the weight of the total composition.

If desired, the composition further contains at least one nonionic surfactant and/or anionic surfactant, whereby the total amount of surfactants present, is in an amount from 0.01 w/w %-15 w/w % of the total composition. Suitably from about 0.01 w/w %-10 w/w % of the total composition.

Typically, nonionic surfactants include, but are not limited to, at least one of an ethoxylates aliphatic alcohols, polyoxyethylene surfactants, polyethylene glycol esters, anhydrosorbitol esters and ethoxylates derivatives thereof, glycol esters, carboxylic amides, monoalkanolamine condensates, polyoxyethylene fatty acid amides or combinations thereof, and the like.

Suitable, examples of at least one nonionic surfactant include, but are not limited to, caprylyl/capryl glucoside, $C_8$-$C_{15}$, ethoxylated alcohol, $C_8$-$C_{14}$ secondary Ethoxylated alcohol 70%, 2-ethyl hexanol EO-PO nonionic surfactants, $C_8$-$C_{14}$ alkylated polyethylene glycol, $C_8$-$C_{14}$ alkylated polypropylene glycol, polyoxyethylene glycol alkylphenol ethers, and glucoside alkyl ethers, polyoxyethylene glycol alkyl ethers, octaethylene glycol monododecyl ether, pentaethylene glycol monododecyl ether, polyoxypropylene glycol alkyl ethers, glucoside alkyl ethers, decyl glucoside, lauryl glucoside, octyl glucoside, polyoxyethylene glycol octylphenol ethers, polyoxyethylene glycol alkylphenol ethers, glycerol alkyl esters, polyglycerol esters, glyceryl laurate, polyoxyethylene glycol sorbitan alkyl esters, sorbitan alkyl esters, dodecyldimethylamine oxide, block copolymers of polyethylene glycol and polypropylene glycol, poloxamers and polyethoxylated tallow amine (POEA), or mixtures thereof, and the like.

Typically, examples of anionic surfactants include, but are not limited to, at least one anionic surfactant includes, but are not limited to, linear alkylbenzene sulfonic acid, alkyl benzene sulfonate, alkyl sulfates/sulfonate, alkanolamide sulfates, ethoxylated alkylphenols, linear alkylbenzene sulphonate, alkyl sulphate, alkoxylated alkyl sulphate, or combinations thereof, and the like.

The composition contains at least one acid including, but not limited to, organic acids, inorganic acids, carboxylic acids, mineral acids, non-surfactant sulfonic acids, or salt thereof, and the like. The total amount of acid present in the composition is from 0.01 w/w %-15 w/w % of the total composition. Suitably, from 0.01 w/w %-10 w/w %; desirably from 0.01 w/w %-5 w/w % for concentrated or ready-to-use form.

Suitably, examples of at least one acid includes, but is not limited to, citric acid, lactic acid, glycolic acid, tataric acid, formic acid, acetic acid, phosphoric acid, oxalic acid, propionic acid, or methane sulfonic acid, butyric acid, pentanoic acid, hexanoic acid, octanoic acid, succinic acid, glutaric acid, adipic acid, benzoic acid, phthalic acid, mixtures thereof, and the like.

Typically the disinfectant composition concentrated form may have a pH of about 0 to about 5; suitably from 1 to about 3. In ready-to-use solution the pH may be from about 0.5 to about 4.5, suitably from 0.5 to 3.

It may be desirable to include one or more additional ingredients in the composition, including but not limited to, biocidal agent, solvent, corrosion inhibitor, emulsifier, fragrance, dye, preservative, anti-foaming agent, thickening agent, hydrotropes agent, second biocide, sequestering/chelating agent, aid stabilizing solubilizer, aqueous solvent, or mixtures thereof, and the like.

If stabilizers and/or chelating agents are added, the stabilizer includes, but is not limited to, peroxide stabilizers, present in an amount from 0.01 w/w %-5 w/w % based on the weight of the total composition.

Typically stabilizers/chelating agents, include but are not limited to, aminocarboxylic acid base products, phosphates and phosphonates, hydroxycarboxylates, polyacrylates, sugar acrylates, polymeric clarifiers, dichlor, trichlor, cyanuric acid, organic and/or inorganic sequestering agents, and the like.

Examples of phosphates sequestering agents include inorganic polyphosphates such as sodium hexametaphosphate (SHMP), sodium polyphosphate, sodium tripolyphosphate, sodium trimetaphosphate, sodium pyrophosphates, combinations thereof, and the like.

Examples of include phosphonated aminopolycarboxylates such as ethylenediamine tetra(methylene phosphonic acid) (EDTMP), Diethylene Triamine Penta Methylene Phosphonic Acid (DETMP), aminotris(methylenephosphonic acid) (ATMP), diethylenetriamine penta(methylene phosphonic acid) (DTPMP), HEDP or salts thereof; combinations thereof, and the like.

Suitably, examples of stabilizers/chelating agents, include, but are not limited to, phosphoric acid, 1-hydroxyethylidenediphosphonic acid (HEDP), phytic acid, am inophosphate, phosphonate and sodium glutamate, $NaH_2PO_4$, $Na_5P_3O_{10}$, organophosphonic acid, amino-phosphonate, silver dihydrogen citrate, diphosphonic acid, ethylenediaminetetraacetic acid (EDTA), N-(hydroxyethyl)-ethylenediaminetriacetic acid (HEDTA), tri(methylene phosphoric acid), diethylenetriaminepenta(methylene phosphoric acid), 2-hydroxy ethylimino bis(ethylene phosphoric acid), citric acid, dipicolinic acid, ethylenediamine-N,N'-disuccinic acid, methylglycinediacetic acid and their alkaline salts thereof, nitriotriacetic acid (NTA), 2-hydroxyethyliminodiacetic acid (HEIDA), and salts thereof, cyclohexane-1,2- diaminotetrakismethylene phosphonic acid or water-sol, diethylenetriamine penta(methylene phosphonic acid), colloidal stannate, diethylenetriamine pentaacetic acid (DTPA), citrate salts, gallate salts, malate salts, malonate salts, oxaloacetate salts, oxalate salts, pyruvate salts, succinate salts, 2-hydroxypyridine-1-oxide (2-HPNO), hyroxyethylidene diphosphonic acid (HEDP) zinc salt, triethanol amine phosphate or mixtures thereof, and the like.

Typically, if a biocidal agent is added to the disinfectant composition; the biocidal agent acts as a second biocidal agent in the composition; whereby the biocidal agent is present in an amount from 0.01%-40 w/w %, or suitably from 0.01 w/w %-25 w/w %, based on the weight of the total composition.

Examples of a second biocidal agents including, but not limited to, halogen-releasing compound; quaternary ammonium compounds (include quaternary ammonium halides, sulfate, phosphate, nitrate, or combinations thereof; such as benzylalkonium chloride), isothiazolones or mixtures thereof, pyrithiones, glutaraldehyde, Iodopropynyl butylcarbamate (IPBC), polyhexamethylene biguanide (PHMB), bronopol, amines (such as Bis (3-aminopropyl) dodecylamine), metal salts, poly(oxyethylene (dimethylimino) ethylene (dimethylimino) ethylene dichloride), sodium dimethyldithiocarbamate, 2-chloro-4,6-bis(ethylamino)-5-triazine, oxidizers, combinations thereof, and the like.

Examples of halogen-releasing compounds include, but not limited to, chlorinated isocyanuric acids or salts thereof, isothiazolinone or a mixture of isothiazolinones; halogenated hydantoins, hypochlorous acids or salts thereof, chlorine gas, chlorine dioxide, hypobromite salts, hypobromous acid; and compatible combinations thereof, and the like; essentially free of any peracid-based solutions, derivatives or salts thereof.

Examples of chlorinated isocyanuric acids or salts thereof, include but not limited to, such as, trichloroisocyanuric acid (TCCA), and dichloroisocyanuric acid (DCCA); dichloroisocyanurate salts (e.g. sodium dichloroisocyanurate, potassium dichloroisocyanurate), trichloroisocyanurate and (e.g. sodium or potassium trichloroisocyanurate), combinations thereof, and the like.

Examples of chlorinated halogenated hydantoins include both chlorine and bromine-containing hydantoins such as bromochlorodimethylhydantoin (BCDMH); dibromodimethylhydantoin (DBDMH), dichlorodimethylhydantoin (DCDMH), dichloromethylethylhydantoin (DCMEH), combinations thereof, and the like.

Examples of hypochlorite salts; hypochlorous or hypobromous acid and salts thereof include, but not limited to, lithium hypochlorite, sodium hypochlorite, potassium hypochlorite, magnesium hypochlorite, calcium hypochlorite, combinations thereof, and the like.

Examples of metal salts include, but are not limited to, zinc chloride, zinc oxide, aluminum sulfate, copper sulphate, copper citrate, copper EDTA (ethylene diaminetetraacetic acid), copper gluconate, colloidal silver, silver nitrate, potassium monopersulfate, sodium perborate, sodium percarbonate, combinations thereof, and the like.

The disinfectant composition as described in the present invention, is concentrate and/or a ready-to use composition; whereby the concentrated composition is diluted with an aqueous solvent, non-aqueous solvent or mixture thereof; to provide a ready-to-use composition for consumer use. Diluted, the hydrogen peroxide source is present in an amount from 0.01 w/w % to 20 w/w %, based on the weight of the total composition. Suitably from 0.1 w/w %-15 w/w %, based on the weight of the total composition; and desirably from 0.1 w/w %-8 w/w %, based on the weight of the total composition.

Typically, the solvent is an aqueous solvent, non-aqueous solvent or mixture thereof, and the like; present in an amount for the total composition to equal 100%. For example, the solvent is a straight or branched chain water soluble alcohol, water.

Examples of aqueous solvent include, but not limited to, water, aqueous alcohols, ammonia water, acid solutions, hydrogen peroxide solution, salt solutions, water-miscible organic solvents, alkanolamines, or glycol ethers, combinations thereof, and the like.

Examples of non-aqueous solvents include, but are not limited to, non-aqueous alcohols, univalent or polyvalent alcohols, alkanolamines, or glycol ethers, any substance immiscible in water, mixtures thereof, and the like.

Suitably, the solvent used is water, an aqueous alcohol, glycol ether, aromatic alcohol or blend thereof.

The disinfectant composition is one having efficacy against one or more micro-organism including, but not limited to, gram positive bacteria, gram negative bacteria, viruses, fungi, mildew, mold or combinations thereof, and the like.

Specifically, whereby the microorganisms include, but are not limited to, *Staphylococcus, Pseudomonas*, hepatitis, rotavirus, rhinovirus, tuberculosis or combinations thereof, and the like.

Desirably, the disinfectant composition has great efficacy against tuberculosis containing bacteria, including but not limited to, *M. terrae*. The composition exhibited a >5 log reduction against *M. terrae* at a contact time of 5 minutes or less. Specifically, whereby the disinfectant composition exhibits a >5 log reduction against *M. terrae* at a contact time of about 3 minutes.

One aspect of the present invention provides a disinfectant composition, as described in the present invention, having a) an effective amount of a hydrogen peroxide source, wherein said source comprises a hydrogen peroxide solution; b) a at least one aromatic alcohol wherein said alcohol comprises, benzyl alcohol and/or phenoxyethanol; c) at least one glycol or glycol ether, wherein said glycol comprises diethylene glycol monobutyl ether, triethylene glycol monobutyl ether; d) at least one nonionic and/or anionic surfactant, wherein said surfactant comprises $C_{12}$-$C_{15}$, Ethoxylated alcohol, $C_{12}$-$C_{14}$ secondary Ethoxylated alcohol 70%, 2-ethyl hexanol EO-PO nonionic surfactant, Caprylyl/Decyl Glucoside, and/or linear alkylbenzene sulfonic acid; and e) at least one acid, wherein said acid comprises methanesulfonic acid; wherein the composition is effective against tuberculosis and/or *M. terrae*.

Another aspect of the present invention provides a method for disinfecting a surface from tuberculosis and/or *M. terrae*, wherein said method comprises adding an effective amount of the disinfectant composition, according to the present invention, to a surface, in an amount to effectively kill a majority of the microbes located on said surface.

The method as described provides a disinfectant composition inhibiting the growth of one or more micro-organisms therein and/or to reduce the number of live micro-organisms. Specifically, whereby the disinfectant composition, according present invention exhibits a >5 log reduction at a contact time of 5 minutes or less. Suitably whereby the disinfectant composition, according to the present invention, exhibits a >5 log reduction at a contact time of 3 minutes.

Typically, a surface is any hard or soft surface including, but are not limited to, a floor, a wall, a countertop, an appliance, a fixture, fabric, textile, upholstery, other hard surfaces, soft surfaces or any surface needed treatment against microorganism; suitably tuberculosis containing bacteria and/or M. terrae.

Examples of soft surfaces include, but are not limited to, upholstery, fabric, upholstered couches, sofas, chairs, seat cushions, upholstered cushions, pillows, upholstered furniture, fabric window treatments, curtains, draperies, shower curtains, fabric gym/laundry/diaper bags, back packs, fabric hampers, fabric dog/pet bedding, blankets, fabric upholstered car seats, fabric stuffed animals, toys, and the like.

For example, the compositions of the invention provided sanitizing or disinfecting properties for hard, non-porous surfaces. The composition of the invention is well suited for disinfecting or sanitizing flooring materials, countertops, ceramic surfaces, metal surfaces, glass surfaces, stone surfaces, and the like.

The compositions can be used to clean the surfaces, destroy microorganisms on the surface and/or prevent growth of microorganisms on the surface. Likewise, the compositions can be used in the food service industry to disinfect and sanitize food processing equipment and other food processing surfaces or to wash produce, such as vegetables. The compositions can also be used in the healthcare industry to disinfect surfaces, facility, equipment and hospital instruments and equipment, and/or disinfect utensils. The compositions can be used in a concentrated or diluted form, depending upon the application.

*Mycobacterium terrae* (*M. terrae*) kill was assessed using the OECD Quantitative Method for Evaluating Bactericidal and Mycobactericidal Activity of Microbicides. The method provides a quantitative assessment of the performance of liquid antimicrobial substances against *M. terrae* designed for use on hard, non-porous surfaces. This method is based on an Organization for Economic Co-operation and Development (OECD) Guidance Document and provides log reduction (LR) as the quantitative measure of efficacy for liquid disinfectants. *M. terrae* $\log_{10}$ reduction is often used as a pre-screening tool to determine potential efficacy on tuberculosis which is generally recognized as harder to kill and more difficult to work with in labs. *M. terrae* $\log_{10}$ reduction was assessed using a 3 minute contact time and 5% soil.

In another aspect, the present invention provides a method for enhancing the disinfectant properties of a hydrogen peroxide source, wherein said method comprises adding a sufficient amount of b) at least one aromatic alcohol; c) at least one glycol or glycol ether; d) at least one nonionic and/or anionic surfactant; and e) at least one acid; with a hydrogen peroxide source and wherein the composition is applied to a surface.

In yet another aspect, the invention provides a disinfection composition comprising b) at least one aromatic alcohol; c) at least one glycol or glycol ether; d) at least one nonionic and/or anionic surfactant; and e) at least one acid; wherein the composition is effective against tuberculosis and/or *M. terrae*; and wherein the composition may be diluted with a solvent to form a ready-to-use composition.

The solvent used to form a ready-to-use composition includes but is not limited to, a hydrogen peroxide source, an aqueous solvent, non-aqueous solvent or mixtures thereof. Examples of such solvents are those as previously described.

In a further aspect, the invention provides a two-part disinfectant, comprising: a first container including a) a biocidal amount of hydrogen peroxide, and a solvent; and a second container including b) at least one aromatic alcohol; c) at least one glycol or glycol ether; d) at least one nonionic and/or anionic surfactant; and e) at least one acid.

Typically, the two-part disinfectant, as described is effective against tuberculosis and/or *M. terrae*, and wherein said disinfectant provides a >5 log reduction at a contact time of 5 minutes or less. Suitably, the two-part disinfectant composition provides a >5 log reduction at a contact time of 3 minutes.

In another aspect, the invention provides an additive for a disinfectant composition comprising b) at least one aromatic alcohol; c) at least one glycol or glycol ether; d) at least one nonionic and/or anionic surfactant; and e) at least one acid; wherein said additive enhances the disinfecting properties of said composition when combined with a disinfecting active.

Typically, the disinfecting active includes, but is not limited to, a hydrogen peroxide solution, alcohol, oxidizer, metal salt, halogen, bleach, phenol, antibiotic cream, pharmaceutically active, astringent, antihistamine, analgesic, skin-cleansing/cleaning agent, antifungal/antimicrobial/antibacterial agent, or essential oil, natural extract, or other active having disinfecting properties, combinations thereof, and the like.

The following examples illustrate the invention without limitation. All parts and percentages are given by weight unless otherwise indicated.

Example 1. Formulations

TABLE 1

| Formulations | | | | | | | | |
|---|---|---|---|---|---|---|---|---|
| | Formulation (w/w %) | | | | | | | |
| Ingredients | 1 | 2 | 3 | 4 | 5 | 6 | 7 | 8 |
| DI Water | 78.56 | 86.56 | 88.57 | 88.06 | 93.92 | 78.56 | 80.56 | 78.556 |
| HP (50%) | 2.33 | 2.33 | 2.31 | 2.33 | 2.30 | 2.33 | 2.33 | 2.334 |
| PA (85%) | 0.53 | 0.53 | 0.53 | 0.53 | 0.53 | 0.53 | 0.53 | 0.530 |
| MSA (70%) | 2.29 | 2.29 | 2.29 | 2.29 | 2.29 | 2.29 | 2.29 | 2.290 |
| Benzyl alcohol | 3.00 | | 2.90 | | | | | |
| Phenoxyethanol | | 1.50 | | | | 3.00 | 2.00 | 3.00 |
| C/D glucoside | | | 1.40 | | | | | |
| ethoxylate alc. $C_{12-15}$ | | | 2.00 | | | | | |
| Nonionic surf. | | | | | 0.67 | | | |
| LAS | | | | | | | | |

TABLE 1-continued Formulations

| Ingredients | Formulation (w/w %) | | | | | | | |
|---|---|---|---|---|---|---|---|---|
| | 1 | 2 | 3 | 4 | 5 | 6 | 7 | 8 |
| EDDS | 0.29 | 0.29 | | 0.29 | 0.29 | 0.29 | 0.29 | 0.29 |
| Ethoxylate alc.* | 3.00 | 1.50 | | 1.50 | | 3.00 | 3.00 | 3.00 |
| DGME | 10.00 | 5.00 | | 5.00 | | 10.00 | 9.00 | |
| TGME | | | | | | | | 10.00 |
| Total | 100.00 | 100.00 | 100.00 | 100.00 | 100.00 | 100.00 | 100.00 | 100.00 |

HP: hydrogen peroxide; PA: phosphoric acid; MSA: methanesulfonic acid; C/D glucoside: caprylyl/decyl glucoside; Nonionic surf.: 2-Ethyl Hexanol EO-PO Nonionic Surfactant; LAS: linear alkylbenzene sulfonic acid; EDDS: Ethylenediamine-N,N'-disuccinic acid (35%); Ethoxylate alc.* $C_{12-14}$ secondary 70%; DGME: diethylene glycol monobutyl ether; TGME: triethylene glycol monobutyl ether.

All formulated solutions in Table 1 can exist as is (ready to use) or can be concentrated in two basic ways which are demonstrated in Table 7 using Formulation 2 as an example. The first way is to simply make, for example but not limited to, a 1:4 concentrate which will be diluted with the appropriate amount of hydrogen peroxide and water.

Formulation 5 in Table 1, is an acidified hydrogen peroxide formulation containing surfactants but no blended solvent was included in the composition, yielding a low *M. terrae* log reduction (see Table 2). Formulation 3 included the ingredients from formula 5 plus the novel solvent blend showing a dramatic increase in *M. terrae* log reduction. Formulation 4 included the ingredients from formula 5 plus only half of the solvent blend Diethylene; showing hardly any *M. terrae* log reduction. Formula 1 contains a blended ratio of the novel solvents in the formula, exhibiting a dramatic increase in *M. terrae* log reduction. Formulation 2 is similar to 4 except that it also contains 1.5% phenoxyethanol which increased *M. terrae* log reduction. Formula 6 is similar to 2 except the phenoxyethanol level was doubled along with the butyl carbitol level and this dramatically increased *M. terrae* log reduction.

It is significant to point out that the solvent blend containing a glycol ether with a phenoxyethanol (Formula 7 and 2) had on increasing effect on the *M. terrae* and TB efficacy. Formula 2 had an even lower level of the solvent blend but managed to pass TB, which is even more unexpected.

Example 2. *M. terrae* OECD Test Method at 3 Min Contact Time

TABLE 2

| Results from *M. terrae* OECD test method | |
|---|---|
| Formula | $Log_{10}$ Reduction on *M. terrae* |
| 1 | 5.02 |
| 2 | 3.41 |
| 3 | 3.87 |
| 4 | 0.62 |
| 5 | 1.20 |
| 6 | 5.02 |

TB was assessed using the AOAC Germicidal Spray Test Tuberculocidal test which involves testing *Mycobacterium bovis* (BCG) ATCC 35743 cultured in 7H11 growth media for 21±2 day at 36±1° C. According to the Regulatory Agency (EPA) guidelines all formulations passed with no visible growth observed in any of the subculture broth tubes per lot, and controls met their stipulated criteria. When tested as described, all formulations passed *Mycobacterium bovis* (BCG), containing a 5% organic soil load at a 3 minute contact. All of the test controls met the criteria established for a valid test.

What is especially surprising, however, is the significant impact that the solvent blend containing a Glycol Ether with a Phenoxyethanol (Formula 7 and 2) had on increasing the *M. terrae* and TB efficacy. Formula 2 had an even lower level of the solvent blend but managed to pass TB which is even more unexpected.

Example 3. TB Assessment (Pass/Fail)

TABLE 3

| TB assessment at 3 min contact time | | |
|---|---|---|
| Formula | Tuberculocidal Effectiveness Test | Pass/Fail |
| 1 | 0/30 | PASS |
| 2 | 0/30 | PASS |
| 7 | 0/30 | PASS |

Example 4. Stability Testing

TABLE 4

| Physical stability testing of the disinfectant composition | | | | | |
|---|---|---|---|---|---|
| | | Formulations | | | |
| Time (wk) | Temp. | 1 | 7 | 2 | 8 |
| 1 | Freezing | Clear-Schlieren Soluble | Clear-Schlieren Soluble | Clear-Schlieren Soluble | Clear-Schlieren Soluble |
| | Refrigerated | Clear | Clear | Clear | Clear |
| | RT | Clear | Clear | Clear | Clear |
| | 40° C. | Clear | Clear | Clear | Clear |
| | 50° C. | Clear | Clear | Clear-slight tint | Clear |
| 2 | Freezing | Clear-Schlieren Soluble | Clear-Schlieren Soluble | Clear-Schlieren Soluble | Clear-Schlieren Soluble |
| | Frig | Clear | Clear | Clear | Clear |
| | RT | Clear | Clear | Clear | Clear |
| | 40° C. | Clear | Clear | Clear | Clear |
| | 50° C. | Clear | Clear-slight tint | Clear-slight tint | Tint |
| 4 | Freezing | Clear-Schlieren Soluble | Clear-Schlieren Soluble | Clear-Schlieren Soluble | Clear-Schlieren Soluble |

TABLE 4-continued Physical stability testing of the disinfectant composition

| | | Formulations | | | |
|---|---|---|---|---|---|
| Time (wk) | Temp. | 1 | 7 | 2 | 8 |
| | Refrigerated | Clear | Clear | Clear | Clear |
| | RT | Clear | Clear | Clear | Clear |
| | 40° C. | Clear | Slight tint | Slight tint | Slight tint |
| | 50° C. | Clear | Light tint | Light tint | Straw |

Formulations 1, 7 and 2 were filled into 4 oz. glass jars with closures and placed into ovens at various controlled temperatures. The samples were pulled at the times and temperatures stated in Table 4 and visually assessed. All samples at the end of 4 weeks were found to have acceptable physical stability.

Example 5. Hydrogen Peroxide Stability

TABLE 5

Hydrogen peroxide stability

| | | Formulation (w/w %) | | | |
|---|---|---|---|---|---|
| | | 1 | 7 | 2 | 8 |
| Time (wk) | Temp | $H_2O_2$ % Loss* | $H_2O_2$ % Loss* | $H_2O_2$ % Loss* | $H_2O_2$ % Loss* |
| 0 | RT | 1.16/0 | 1.16/0 | 1.16/0 | 1.14/0 |
| 1 | 50° C. | 1.15/0.86 | 1.15/0.86 | 1.15/0.86 | 1.11/2.63 |
| 2 | 50° C. | 1.11/4.3 | 1.11/4.3 | 1.11/4.3 | 1.12/1.75 |
| 4 | 50° C. | 1.1/5.17 | 1.09/6.03 | 1.1/5.17 | 1.08/5.26 |

The same formulations tested in Table 4 were tested for $H_2O_2$ stability at 50° C. for 4 wk (see Table 5). All formulations had fairly good peroxide stability with none exceeding a 6 w/w % drop in $H_2O_2$ at 4 wk at 50° C.

Calculating percent hydrogen peroxide loss: % Loss of $H_2O_2$=(Initial amount of $H_2O_2$—amount of $H_2O_2$ after storage)/Initial amount of $H_2O_2$ and multiply result by 100.

Example 6. AOAC Germicidal Spray Method for Hard Surface Disinfection

TABLE 6

AOAC Germicidal Spray Method for Hard Surface Disinfection

| Batch | P. aeruginosa (ATCC 15442) | S. aureus (ATCC 6538) | S. enterica (ATCC 10708) | Pass/Fail |
|---|---|---|---|---|
| A | 0/60 | 0/60 | 0/60 | PASS |
| B | 0/60 | 1/60 | 0/60 | PASS |
| C | 0/60 | 0/60 | 0/60 | PASS |

Formulation 2 was micro tested against *S. enterica*, *S. aureus* and *P. aeruginosa* using the AOAC Germicidal Spray Method for Hard Surface Disinfection under GLP conditions using soil load of 5% (Fetal Bovine Serum) and a 1 minute contact time (see Table 6). Formulation 2 passed against all 3 organisms under GLP conditions.

Example 7. Formulation #2

TABLE 7

Formulation # 2 comparison (w/w %)

| | Solvent pack A | Conc. A | Conc. B |
|---|---|---|---|
| DI Water | — | 44.45 | 53.90 |
| Phosphoric Acid (85%) | — | 2.65 | 5.30 |
| Methanesulfonic Acid (70%) | — | 11.45 | 22.90 |
| Ethylenediamine-N,N'-disuccinic acid (35%) | — | 1.45 | 2.90 |
| Alcohols, $C_{12}$-$C_{14}$ secondary, ethoxylated (70%) | — | 7.5 | 15.0 |
| Phenoxyethanol | 23.1 | 7.5 | — |
| diethylene glycol monobutyl ether | 76.9 | 25 | — |
| Total | 100.00 | 100.00 | 100.00 |

All formulated solutions in Table 1 can exist as is (ready to use) or can be concentrated in two basic ways which are demonstrated in Table 7 using Formulation 2 as an example. The first way is to simply make, for example but not limited to, a 1:4 concentrate which will be diluted with the appropriate amount of hydrogen peroxide and water.

Example 8. Formulation #2 Concentrate Pack Formulation

TABLE 8

Concentrate A and B pack formulation comparison

| Ingredients | RTU prepared from Concentrate A | RTU prepared from Concentrate B & solvent pack |
|---|---|---|
| DI Water | 77.67 | 81.17 |
| Hydrogen Peroxide (50%) | 2.33 | 2.33 |
| Concentrate A | 20.0 | — |
| Concentrate B | — | 10.00 |
| Solvent Pack | — | 6.50 |
| Total | 100.00 | 100.00 |

The second way is similar to the first way except instead of just removing hydrogen peroxide from the concentrate, the two solvents are removed as well (Table 7). So the concentrate would be diluted with water, hydrogen peroxide and/or a solvent pack containing the diethylene glycol monobutyl ether and phenoxyethanol (Table 8).

It will be understood that each of the elements described in the examples above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims.

The foregoing embodiments are presented by way of example only; the scope of the present disclosure is to be limited only by the following claims.

While the invention has been described above with references to specific embodiments thereof, it is apparent that many changes, modifications and variations can be made without departing from the invention concept disclosed herein. Accordingly, it is intended to embrace all such changes, modifications, and variations that fall within the spirit and broad scope of the appended claims.

What is claimed is:

1. A disinfectant composition comprising
   a) an effective amount of a hydrogen peroxide source,
   b) at least one aromatic alcohol,
   c) at least one glycol or glycol ether,
   d) at least one nonionic and/or anionic surfactant, and
   e) at least one acid,
   wherein the at least one aromatic alcohol comprises phenoxyethanol.

2. The disinfectant composition, according to claim 1, wherein hydrogen peroxide source comprises a hydrogen peroxide solution, sodium percarbonate, potassium percarbonate, sodium perborate, potassium perborate, hydrogen peroxide urea or peroxide salts, hydrated salts thereof, or combinations thereof, wherein the concentration of the hydrogen peroxide source is from 0.01 w/w % to about 90 w/w %, of the total weight of the composition.

3. The disinfectant composition, according to claim 1, wherein the at least one aromatic alcohol is present in an amount from about 0.01 w/w %-50 w/w %, of the total weight of the composition.

4. The disinfectant composition, according to claim 1, wherein at least one glycol or glycol ether comprises ethylene glycol, propylene glycol, butylene glycol, diethylene glycol propyl ether, ethylene glycol monomethyl ether, ethylene glycol monoethyl ether, ethylene glycol monopropyl ether, ethylene glycol monoisopropyl ether, ethylene glycol monobutyl ether, diethylene glycol monomethyl ether, diethylene glycol monobutyl ether, diethylene glycol monoethyl ether, diethylene glycol mono-n-butyl ether, ethylene glycol dimethyl ether, ethylene glycol diethyl ether, ethylene glycol dibutyl ether, propylene glycol n-butyl ether, tripropylene glycol methyl ether, dipropylene glycol methyl ether, dipropylene glycol butyl ether, triethylene glycol monobutyl ether, or combinations thereof, present in an amount from about 0.01 w/w %-50 w/w % of the total composition.

5. The disinfectant composition, according to claim 1, wherein at least one aromatic alcohol and at least one glycol or glycol ether is present as a blend and wherein the blend is in a ratio of 1:100 to 100:1, wherein the blend of at least one aromatic alcohol and at least one glycol or glycol ether is present in an amount from about 0.01 w/w %-90 w/w % of the total composition.

6. The disinfectant composition, according to claim 1, wherein the at least one non-ionic surfactant and/or anionic surfactant comprises ethoxylated aliphatic alcohols, polyoxyethylene surfactants, polyethylene glycol esters, anhydrosorbitol esters and ethoxylates derivatives thereof, glycol esters, carboxylic amides, monoalkanolamine condensates, polyoxyethylene fatty acid amides, linear alkylbenzene sulfonic acid, alkyl sulfates, alkanolamide sulfates, ethoxylated alkylphenols or combinations thereof, and wherein the total amount of surfactants present is in an amount from 0.01 w/w %-15 w/w % of the total composition.

7. The disinfectant composition, according to claim 6, wherein the nonionic surfactant comprises caprylyl/capryl glucoside, $C_{12}$-$C_{15}$, ethoxylated alcohol, $C_{12}$-$C_{14}$ secondary Ethoxylated alcohol 70%, 2-ethyl hexanol EO-PO nonionic surfactant, or combinations thereof.

8. The disinfectant composition, according to claim 1, wherein at least one acid comprises an organic acid, inorganic acid, carboxylic acid, mineral acid, non-surfactant sulfonic acid, or salt thereof, wherein the total amount of the acids is from 0.01 w/w %-15 w/w % of the total composition.

9. The disinfectant composition, according to claim 8, wherein at least one acid comprises citric acid, lactic acid, glycolic acid, tataric acid, formic acid, acetic acid, phosphoric acid, oxalic acid, propionic acid, or methane sulfonic acid.

10. The disinfectant composition, according to claim 1, further comprising a straight or branched chain water soluble alcohol.

11. The disinfectant composition, according to claim 1, further comprising a peroxide stabilizer and/or chelating agent; wherein said stabilizer and/or chelating agent is present in an amount from 0.01 w/w %-5 w/w % based on the weight of the total composition.

12. The disinfectant composition, according to claim 1, wherein the composition has a pH of about 0 to about 5.

13. The disinfectant composition, according to claim 1, further comprising a second biocidal agent present in an amount from 0.01 w/w %-40 w/w %.

14. The disinfectant composition, according to claim 1, wherein the composition is a concentrate.

15. The disinfectant composition, according to claim 1, wherein the composition provides an effective kill of >5 log reduction at contact time of 5 minutes or less against one or more micro-organism comprising gram positive bacteria, gram negative bacteria, viruses, fungi, mildew, mold or combinations thereof.

16. The disinfectant composition, according to claim 15, wherein the microorganism comprises *Staphylococcus*, *Pseudomonas*, hepatitis, rotavirus, rhinovirus, tuberculosis, *M. terrae* or combinations thereof.

17. The disinfectant composition, according to claim 1, comprising
   a) an effective amount of a hydrogen peroxide source, wherein said source comprises a hydrogen peroxide solution;
   b) at least one aromatic alcohol wherein said alcohol comprises, benzyl alcohol and/or phenoxyethanol;
   c) at least one glycol or glycol ether, wherein said glycol comprises diethylene glycol monobutyl ether;
   d) at least one nonionic and/or anionic surfactant, wherein said surfactant comprises $C_{12}$-$C_{15}$, Ethoxylated alcohol, $C_{12}$-$C_{14}$ secondary Ethoxylated alcohol 70%, 2-ethyl hexanol EO-PO nonionic surfactant, Caprylyl/Decyl Glucoside, and/or linear alkylbenzene sulfonic acid; and e) at least one acid, wherein said acid comprises methanesulfonic acid; and wherein the composition is effective against tuberculosis and/or *M. terrae*.

18. A method for enhancing the disinfectant properties of a hydrogen peroxide source, wherein the method comprises adding a sufficient amount of a composition to the hydrogen peroxide source, the composition comprising a) at least one aromatic alcohol; b) at least one glycol or glycol ether; c) at least one nonionic and/or anionic surfactant; and d) at least one acid; with a hydrogen peroxide source, wherein the composition is applied to a surface, and wherein the at least one aromatic alcohol comprises phenoxyethanol.

19. The method according to claim 18, wherein the disinfectant composition provides a >5 log reduction at a contact time of 5 minutes or less.

20. The method according to claim 18, wherein the surface comprises a floor, a wall, a countertop, an appliance, a fixture, fabric, textile, or other hard or soft surface.

21. The method of claim 18, wherein said method comprises applying an effective amount of the disinfectant composition to the surface in an amount to effectively kill a majority of the microbes located on said surface.

22. The method of claim 18, wherein said method comprises disinfecting the surface from tuberculosis and/or *M. terrae*.

23. A two-part disinfectant, comprising:
a first container including
a) a biocidal amount of hydrogen peroxide, and
a solvent; and
a second container including
b) at least one aromatic alcohol;
c) at least one glycol or glycol ether;
d) at least one nonionic and/or anionic surfactant; and
e) at least one acid,
wherein the at least one aromatic alcohol comprises phenoxyethanol.

24. The two-part disinfectant, according to claim 23, wherein said disinfectant is effective against tuberculosis and/or *M. terrae*, and wherein said disinfectant provides a >5 log reduction at a contact time of 5 minutes or less.

* * * * *